(12) United States Patent
Liu et al.

(10) Patent No.: US 10,435,759 B2
(45) Date of Patent: Oct. 8, 2019

(54) HMG1 GENE AND USES THEREOF IN MICROSPORIDIUM MOLECULAR DETECTION

(71) Applicant: SOUTH CHINA AGRICULTURAL UNIVERSITY, Guangdong (CN)

(72) Inventors: Jiping Liu, Guangdong (CN); Xiaojing Song, Guangdong (CN); Wei Cheng, Guangdong (CN)

(73) Assignee: SOUTH CHINA AGRICULTURAL UNIVERSITY, Guangdong (CN)

( * ) Notice: Subject to any disclaimer, the term of this patent is extended or adjusted under 35 U.S.C. 154(b) by 235 days.

(21) Appl. No.: 15/310,783

(22) PCT Filed: Aug. 28, 2015

(86) PCT No.: PCT/CN2015/088443
§ 371 (c)(1),
(2) Date: Nov. 14, 2016

(87) PCT Pub. No.: WO2016/090965
PCT Pub. Date: Jun. 16, 2016

(65) Prior Publication Data
US 2017/0101689 A1    Apr. 13, 2017

(30) Foreign Application Priority Data

Dec. 11, 2014  (CN) .......................... 2014 1 0755669
Dec. 11, 2014  (CN) .......................... 2014 1 0755670

(51) Int. Cl.
*C12Q 1/68*      (2018.01)
*C12Q 1/6895*    (2018.01)
*C12Q 1/6893*    (2018.01)

(52) U.S. Cl.
CPC ......... *C12Q 1/6895* (2013.01); *C12Q 1/6893* (2013.01); *C12Q 2600/158* (2013.01)

(58) Field of Classification Search
CPC ............ C12Q 1/6895; C12Q 2600/158; C12Q 1/6893

USPC ........................................................ 435/91.2
See application file for complete search history.

(56) References Cited

FOREIGN PATENT DOCUMENTS

| CN | 101935707 | 1/2011 |
| CN | 102260737 | 11/2011 |
| CN | 104017890 | 9/2014 |
| CN | 104498509 | 4/2015 |
| CN | 104498599 | 4/2015 |

OTHER PUBLICATIONS

Pan et al., BMC genomiocs, 14: 186, Mar. 1-14, (Year: 2013).*
Bigliardi et al., "Cell biology and invasion of the microsporidia," Microbes and Infection, Apr. 2001, pp. 373-379.
Pei et al., "Diversity of 16S rRNA Genes within Individual Prokaryotic Genomes," Applied and Environmental Microbiology, Jun. 2010, pp. 3886-3897.
Terry et al., "Widespread vertical transmission and associated host sex-ratio distortion within the eukaryotic phylum Microspora," Proc. R. Soc. Lond. B, Jul. 2004, pp. 1783-1789.
Cai et al., "A Protocol for Fast and Efficient Preparation of Genomic DNA and Total Proteins of Nosema bombycis," Science of Sericulture, Sep. 2011, pp. 1019-1024.
"International Search Report (Form PCT/ISA/210)", dated Nov. 17, 2015, with English translation thereof, pp. 1-4.

* cited by examiner

*Primary Examiner* — Cynthia B Wilder
(74) *Attorney, Agent, or Firm* — JCIPRNET

(57) ABSTRACT

The present invention disclosed a *Nosema bombycis* HMG1 gene, a specific primer set used for rapidly detecting *Nosema bombycis*, a group of microsporidium universal detection primers, and uses thereof. The primer set comprises a primer HMG1-sF and a primer HMG1-sR, and nucleotide sequences of the primers are shown in SEQ ID No. 5-6 respectively. The universal detection primers comprise a primer HMG1F and a primer HMG1R, and nucleotide sequences of the primers are shown in SEQ ID No. 3-4 respectively.

1 Claim, 7 Drawing Sheets
Specification includes a Sequence Listing.

SEQUENCE LISTING

<160> NUMBER OF SEQ ID NOS: 8

<210> SEQ ID NO 1
<211> LENGTH: 1136
<212> TYPE: DNA
<213> ORGANISM: Unknown
<220> FEATURE:
<223> OTHER INFORMATION: HMG1 gene DNA sequence

<400> SEQUENCE: 1

```
ttccgaaata atcttctttt aattgattta aattattttt gacctttttgt gaattagatc      60
ttaaattttc atcatccttg tattttttcct gtaaaaaatc agaccatttc tttaacggtt     120
tgatttcaaa accgttttta attaaaagct tgataatttt ggttggagct tcgtaaaatt     180
ttctataatt ggcgtctttg ttcatttttta aggaaggagg ggggagggggc attctataag    240
aaaaattctt ataacgggcg tcttgcatat tattatttga ataacgggc acacgaacag      300
taggataatg aaggagttta taaaacaac cgacaaaaat attactgcct tttttaagtt      360
aaataacata cattcgggtc ttcttataag attcgtttaa atctactctt cctacctttt     420
ttgttatatt ttttcttact acgtatttgt ttcatctctt tttattaacc aatcctttta     480
ctctaattct tttactttcc ccatacacat cttttttatta cttcattcgt catttttta    540
actgttttc agatttttt tctcccctaa atgactgctc aaaaagacga tacggctatt      600
aagaagagac agacggccaa aaagccaaag gacaaaaatg caccaaaaccc cccattaacc    660
ccctatttac gattcggtgc acaacaaagg gcagccgata aaactataac agctcttcct    720
gttgctaaac aagggaaagt tcttgctgaa atgtggagta aattaagtga tgaagcaaaa    780
aataaattta agaagaata cactgaagag aaagcgattt atgataaaaa ttatgaagaa     840
tacaagaaga cggatgatta taaaaagtat caagaccttc ttaaatccct aggaactttt    900
aaagagaaga aaaccaaaag acaatcagct tataatgtgt attataaaga acagtacggg    960
ataatagcca gtaaaactaa aggacttgag atgaaagata taacggctat tattgtaaaa  1020
aactggaagg agattgatga accaaccaaa agatttatg ctgaaaaagc gaaaaaagct   1080
aatgatctta ataaggaaaa taaggagaa gtaggagata gtgatgaata aaagga       1136
```

<210> SEQ ID NO 2
<211> LENGTH: 561
<212> TYPE: DNA
<213> ORGANISM: Artificial Sequence
<220> FEATURE:
<223> OTHER INFORMATION: HMG1 gene cDNA sequence

<400> SEQUENCE: 2

```
atgactgctc aaaaagacga tacggctatt aagaagagac agacggccaa aaagccaaag      60
gacaaaaatg caccaaaaccc cccattaacc ccctatttac gattcggtgc acaacaaagg    120
gcagccgata aaactataac agctcttcct gttgctaaac aagggaaagt tcttgctgaa    180
atgtggagta aattaagtga tgaagcaaaa aataaattta agaagaata cactgaagag    240
aaagcgattt atgataaaaa ttatgaagaa tacaagaaga cggatgatta taaaaagtat   300
caagaccttc ttaaatccct aggaactttt aaagagaaga aaaccaaaag acaatcagct    360
tataatgtgt attataaaga acagtacggg ataatagcca gtaaaactaa aggacttgag   420
atgaaagata taacggctat tattgtaaaa aactggaagg agattgatga accaaccaaa   480
agatttatg ctgaaaaagc gaaaaaagct aatgatctta ataaggaaaa taaggagaa     540
gtaggagata gtgatgaata a                                              561
```

<210> SEQ ID NO 3
<211> LENGTH: 23
<212> TYPE: DNA
<213> ORGANISM: Artificial Sequence
<220> FEATURE:
<223> OTHER INFORMATION: Upstream primer HMG1F

<400> SEQUENCE: 3

```
atgactgctc aaaaagacga tac                                            23

<210> SEQ ID NO 4
<211> LENGTH: 25
<212> TYPE: DNA
<213> ORGANISM: Artificial Sequence
<220> FEATURE:
<223> OTHER INFORMATION: Downstream primer HMG1R

<400> SEQUENCE: 4
ttattcatca ctatctccta cttct                                          25

<210> SEQ ID NO 5
<211> LENGTH: 25
<212> TYPE: DNA
<213> ORGANISM: Artificial Sequence
<220> FEATURE:
<223> OTHER INFORMATION: Upstream primer HMG1-sF

<400> SEQUENCE: 5
ttccgaaata atcttctttt aattg                                          25

<210> SEQ ID NO 6
<211> LENGTH: 22
<212> TYPE: DNA
<213> ORGANISM: Artificial Sequence
<220> FEATURE:
<223> OTHER INFORMATION: Downstream primer HMG1-sR

<400> SEQUENCE: 6
ttgtgcaccg aatcgtaaat ag                                             22

<210> SEQ ID NO 7
<211> LENGTH: 24
<212> TYPE: DNA
<213> ORGANISM: Artificial Sequence
<220> FEATURE:
<223> OTHER INFORMATION: Upstream primer HMG1-xF

<400> SEQUENCE: 7
tccctaggaa cttttaaaga gaag                                           24

<210> SEQ ID NO 8
<211> LENGTH: 24
<212> TYPE: DNA
<213> ORGANISM: Artificial Sequence
<220> FEATURE:
<223> OTHER INFORMATION: Downstream primer HMG1-xR

<400> SEQUENCE: 8
tccttttatt catcactatc tcct                                           24
```

HMG1 GENE AND USES THEREOF IN MICROSPORIDIUM MOLECULAR DETECTION

CROSS-REFERENCE TO RELATED APPLICATION

This application is a 371 application of International PCT application serial no. PCT/CN2015/088443, filed on Aug. 28, 2015, which claims the priority benefit of Chinese application no. 201410755670.4, filed on Dec. 11, 2014, and Chinese application no. 201410755669.1, filed on Dec. 11, 2014. The entirety of each of the above-mentioned patent applications is hereby incorporated by reference herein and made a part of this specification.

TECHNICAL FIELD

The present invention concerns the technical field of entomopathogen molecular detection and more specifically, concerns HMG1 gene and uses thereof in microsporidium molecular detection.

BACKGROUND OF THE PRESENT INVENTION

Research on pebrine (also called silkworm microsporidiosis) started with the pebrine epidemic all over France in 1845. Louis Pasteur associated the "particle" that he observed as the causative factor of pebrine, and then Balbiani identified it as *Nosema bombycis* (J. V. Maddox et al., 2000). There are two routes of infection for *Nosema bombycis*, i.e. horizontal transmission and vertical transmission, wherein the vertical transmission causes huge harm to silkworm eggs production in sericulture and makes considerable negative effects on yield and quality of cocoon in silkworm cocoon production at the same time, which seriously affected the development of downstream economy in the silk industry chain (S. F. Cai, et al., 2011). Subsequent to the nationwide outspreading of pebrine in France, *Nosema bombycis* has always been a significant detection item in silkworm eggs production in various countries as well as import and export trade. In late $19^{th}$ century, the period that sericulture in Japan was most developed, "Female Moth Microscopic Examination Regulations" and "Silkworm Disease Prevention Regulations" were listed into the Japanese Constitution (Takeshi Kawarabata, 2003). In China, pebrine has been listed as Class II diseases in quarantine of imported and exported animals (*List of Infectious and Parasitic Diseases of Imported Animals for Class I and Class II of P.R.C.,* 1992, Agri. (Quarantine) No. 12) as well.

At first, people distinguished *Nosema bombycis* mainly according to the clinical characters of pebrine by visual inspection. After microscope was invented, people detected *Nosema bombycis* according to its morphology and size by microscopic examination, which enhanced the sensitivity and efficiency of detection to a certain extent, and thus the pebrine pandemic in France was restrained and the worldwide sericulture was rescued. However, there are some obvious drawbacks in microscopic examination, such as the high demands for skills and experiences of operating personnel, and *Nosema bombycis* being so tiny that it is difficult to distinguish microsporidium and its analogues due to low specificity and sensitivity of the detection method through general microscopic examination, and especially, *Nosema bombycis* in silkworm egg is generally immature spores which are hardly identified and determined by general optical microscope.

Following the development of PCR (Polymerase Chain Reaction) technology, PCR methods have been used for detecting *Nosema bombycis*, which reaches a higher sensitivity. "Molecular clock" is an effective measure for analysis of biological system evolution on the molecular level, and SSU rRNA (16S rDNA) is a commonly used "molecular clock" in the researches on microorganism evolution (Pei A. Y., et al., 2010). Most of the target genes, at which the primers designed in the researches of PCR detection technology for detecting pebrine aim, are SSU rRNA, but there are very few reports about the primers aiming at other microsporidium genes as much less primers are designed or with low sensitivity. PCR primers V1f/530r, designed by Baker et al. (1995) and Terry et al. (1999) according to the highly conserved sequences of SSU rRNA of closely related species of microsporidium, may identify specific bands of DNA templates in various species of microsporidiums with amplification about 450 bp, but without specificity to *Nosema bombycis*. Also present inventors found that the sensitivity of detection was extremely low when using the above-mentioned primers to detect microsporidium in silkworm eggs, which implied that a suppression factor might exist in silkworm egg extract and interfered with the PCR amplification of *Nosema bombycis* (N.b) DNA. Microsporidium is parasitic in silkworm egg, but the content of the egg is apparently higher than that of the microsporidium to be detected. DNAs of both silkworm eggs and microsporidium exist in the extracted DNA sample, so that silkworm eggs DNAs seriously interfere with the detection of the microsporidium DNAs. Thus, higher requirements are needed for direct detection of microsporidium when using silkworm egg DNA as a template.

Besides, in practical works, particularly in quarantine works, detection of various pathogens of microsporidium in samples is so important that no omission or false detection is allowed. Thus, it is desirable to have a primer set for universal detection of various microsporidiums with excellent detective sensitivity, which is also highly sensitive when using silkworm egg DNA as a template, and such primer set is valuable in extensive applications and of significance in practical detection works of microsporidium.

SUMMARY OF THE PRESENT INVENTION

The technical problem to be solved by the present invention is directed to solve certain issues existing in the current microsporidium detection technology. Specific detection primers for *Nosema bombycis* as well as universal detection primers for various microsporidiums using *Nosema bombycis* HMG1 gene as a target gene are designed. The specific detection primers may be obtained using silkworm DNA/cDNA, silkworm egg DNA/cDNA or silkworm mid-gut DNA/cDNA as templates, with reliable detection results, easy (simple and rapid) operation with strong specificity as well as high sensitivity, which are suitable for rapid detection of *Nosema bombycis*, particularly for the detection of early infection and rapid detection of *Nosema bombycis* in silkworm egg. The universal detection primers can simultaneously detect various microsporidium, such as *Nosema bombycis, Nosema antheraeae, Nosema furnacalis*, in samples with reliable and highly sensitive detection results.

An objective of the present invention is to provide a *Nosema bombycis* HMG1 gene.

Another objective of the present invention is to provide a primer set using *Nosema bombycis* HMG1 gene as a target gene for rapid detection of *Nosema bombycis* and a preparative test kit for *Nosema bombycis*.

Another objective of the present invention is to provide a group of universal detection primers for microsporidium molecular and a universal test kit for microsporidium.

The above-mentioned objectives of present invention can be realized by the technical solutions described below:

A *Nosema bombycis* HMG1 gene, wherein a DNA full-length nucleotide sequence of it is shown in SEQ ID NO:1 and a cDNA full-length nucleotide sequence of it is shown in SEQ ID NO:2.

Based on the research, analysis and summary of the *Nosema bombycis* HMG1 gene, the present inventors have chosen HMG1 gene as a target gene for detection, and have respectively designed specific detection primers for *Nosema bombycis* as well as universal detection primers for various microsporidiums, which are described herein below:

Firstly, a primer set using HMG1 gene as the target gene for rapid detection of *Nosema bombycis*, wherein the primer set comprises an upstream primer HMG1-sF of which nucleotide sequence is shown in SEQ ID NO:5 and a downstream primer HMG1-sR of which nucleotide sequence is shown in SEQ ID NO:6. The primers are sensitive, rapid and highly specific so that *Nosema bombycis* can be detected effectively and specifically according to the present primers, and in particular for the detection of early infection and rapid detection of *Nosema bombycis* in silkworm eggs, the primers have important significance.

The present invention also provides a use of the primer set for rapid detection of *Nosema bombycis* in preparation of a *Nosema bombycis* test kit. It also provides a *Nosema bombycis* test kit comprising an upstream primer HMG1-sF of which its nucleotide sequence is shown in SEQ ID NO:5 and a downstream primer HMG1-sR of which its nucleotide sequence is shown in SEQ ID NO:6.

Preferably, a usage of the test kit is as follows:

Using silkworm DNA/cDNA, silkworm egg DNA/cDNA or silkworm mid-gut DNA/cDNA as templates, a PCR reaction is proceeded by primers HMG1-sF and HMG1-sR, followed by gel electrophoresis to detect amplification products and result determination according to the amplification of DNA fragments. The standard of the result determination is that: specific 684 bp DNA fragments products appear on an agarose gel, which indicates that such silkworm or silkworm egg is infected by *Nosema bombycis*.

Preferably, a reaction system of the PCR reaction is as follows:

| | |
|---|---|
| 2× reaction buffer | 10 µL |
| 10 µM primer HMG1-sF | 0.5 µL |
| 10 µM primer HMG1-sR | 0.5 µL |
| DNA template | 1 µL |
| ddH$_2$O | used to fill the system up to 20 µL; |

Wherein, 2×reaction buffer comprises Taq DNA polymerase, 160 mM Tris-HCl, 40 mM (NH$_4$)$_2$SO$_4$, 3.0 mM MgCl$_2$ and 400 µM dNTP.

Preferably, a procedure of the PCR reaction is as follows: 94° C. for 5 min; 94° C. for 30 s, 50° C. for 45 s, 72° C. for 45 s, 32 cycles; 72° C. for 10 min.

Secondly, a group of universal detection primers for microsporidium, wherein the universal detection primers comprise an upstream primer HMG1F of which its nucleotide sequence is shown in SEQ ID NO:3 and a downstream primer HMG1R of which its nucleotide sequence is shown in SEQ ID NO:4.

Based on obtaining *Nosema bombycis* HMG1 gene (DNA full-length nucleotide sequence of HMG1 gene is shown as SEQ ID NO:1 and cDNA full-length nucleotide sequence thereof is shown as SEQ ID NO:2), the described universal detection primers for microsporidium are designed in the present invention using HMG1 gene as target gene. The primers can universally detect various microsporidiums with great detecting sensitivity, and have extensive application value and significance in practical detection of microsporidium. The primers are particularly suitable for simultaneous detection of *Nosema bombycis, Nosema antheraeae* and *Nosema furnacalis*.

The present invention also provides a use of the universal detection primers for microsporidium in preparation of a universal test kit for microsporidium, and it provides a universal test kit for microsporidium, which comprises the upstream primer HMG1F of which its nucleotide sequence is shown in SEQ ID NO:3 and the downstream primer HMG1R of which its nucleotide sequence is shown in SEQ ID NO:4.

Preferably, a usage of the test kit is as follows:

Using sample DNA or cDNA as template, a PCR reaction is proceeded with primers HMG1F and HMG1R, followed by gel electrophoresis to detect amplification products and result determination according to the amplification of DNA fragments. The standard of the result determination is that: specific 561 bp DNA fragments products appear on an agarose gel, which indicates that such sample is infected by *Nosema bombycis*.

Preferably, a reaction system of the PCR reaction is as follows:

| | |
|---|---|
| 2× reaction buffer | 10 µL |
| 10 µM upstream primer HMG1F | 0.5 µL |
| 10 µM downstream primer HMG1R | 0.5 µL |
| DNA template | 1 µL |
| ddH$_2$O | used to fill the system up to 20 µL; |

Wherein, 2×reaction buffer comprises Taq DNA polymerase, 160 mM Tris-HCl, 40 mM (NH$_4$)$_2$SO$_4$, 3.0 mM MgCl$_2$ and 400 µM dNTP.

Preferably, a procedure of the PCR reaction is as follows: 94° C. for 5 min; 94° C. for 30 s, 58.5° C. for 45 s, 72° C. for 45 s, 32 cycles; 72° C. for 10 min.

The present invention has following beneficial effects:

For the first time, the full-length sequences of DNA and cDNA from *Nosema bombycis* HMG1 gene are cloned in the present invention. Based on these, a primer set for rapid detection of *Nosema bombycis* with excellent specificity and sensitivity is designed. The primer can be used for PCR detection of silkworm microsporidiosis, can detect *Nosema bombycis* in samples accurately, and may provide guarantee for detection of infected silkworm eggs (i.e. silkworm eggs infected by microsporidium or *N. bombycis*) in silkworm eggs production and for safe distribution of silkworm eggs.

A group of universal detection primers for microsporidium are also designed in the present invention based on HMG1 gene. The primers can be used for PCR detection of silkworm microsporidiosis with great universality and sensitivity. The primers can detect various microsporidiums universally, have great detecting sensitivity, and have extensive application value and significance in practical detection of microsporidium.

In additional, primers and associated reagents in the present invention can be assembled into a kit for convenient use. Furthermore, suitable PCR amplification templates are various and have a wide range of application, which can be either DNA or cDNA of samples, and DNA of silkworm eggs can be used as templates directly. Specific detection primers for *Nosema bombycis* can also use silkworm DNA/cDNA, silkworm egg DNA/cDNA or silkworm mid-gut DNA/cDNA as templates, which greatly increases the range of detection objects.

More importantly, two kinds of detection primers and the kit in the present invention can be used to specifically detect microsporidium in early infection, which provide a rapid detection method for early detection of microsporidiosis or pebrine.

DETAILED DESCRIPTION OF THE PREFERRED EMBODIMENT

Figure 1:
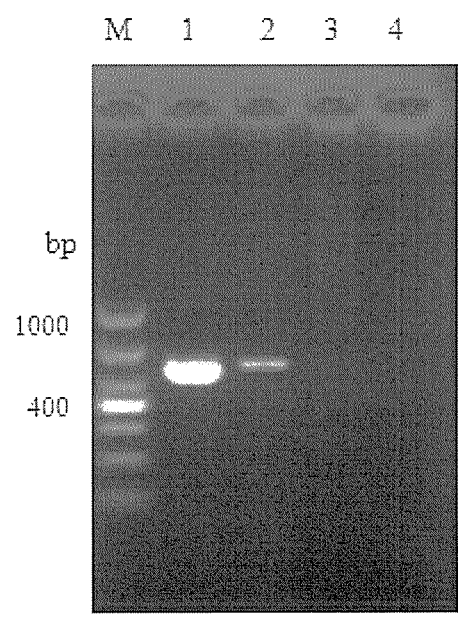
FIG. 1 shows the detection results of HMG1F/HMG1R primers. Lane: M: DL1000, 1: infected silkworm egg DNA, 2: purified *Nosema bombycis* (N.b) DNA, 3: (healthy) pebrine-free silkworm egg DNA, 4: ddH$_2$O.

The present invention will be further described below in combination with accompanied drawings and specific embodiments which are not intended to limit the present invention in any manner. Unless otherwise specified, reagents, methods and equipment used in the present invention are conventional reagents, methods and equipment in present technical field.

Unless otherwise specified, reagents and materials used in the embodiments below are commercially available.

Embodiment 1. *Nosema bombycis* HMG1 Gene

1. According to the gene homologous clone method in gene cloning technology of molecular biology, the full-length sequences of cDNA and DNA in *Nosema bombycis* HMG1 gene were obtained by cloning.

2. The specific method of obtaining the full-length sequence of cDNA is described herein below:

(1), Primers HMG1F/HMG1R were designed via Primer premier 5.0 software in combination with comprehensive analysis. The sequences thereof are shown in SEQ ID NO:3 and SEQ ID NO:4.

```
Upstream primer HMG1F (SEQ ID NO: 3):
5' ATGACTGCTCAAAAAGACGATAC 3'

Downstream primer HMG1R (SEQ ID NO: 4):
5' TTATTCATCACTATCTCCTACTTCT 3'
```

(2) Using purified *Nosema bombycis* (N.b) spores DNA as template, PCR amplification was conducted with the set of primer HMG1F/HMG1R.

(3) PCR products were connected to pMD19T after purification, followed by the conversion into *E. coli* DH-5a for culture.

(4) After the recombinant plasmid was extracted and sequenced, the full-length sequence of cDNA in HMG1 gene was obtained and shown as SEQ ID NO:2.

3. Acquisition of full-length sequence of DNA

Via genome high-throughput sequencing method, after abundant BLAST analysis of gene prediction, and finally after PCR sequencing verification, the full-length sequence of DNA in *Nosema bombycis* HMG1 gene was obtained and shown in SEQ ID NO: 1.

4. According to several confirmations of sequencing results, the full-length sequence of DNA in *Nosema bombycis* HMG1 gene was obtained and shown in SEQ ID NO:1, and the full-length nucleotide sequence of cDNA thereof is shown in SEQ ID NO:2.

Embodiment 2. Design of Detection Primers and Establishment of PCR Amplification Method 1. Design of Primers Based on the acquisition of *Nosema bombycis* HMG1 gene, several pairs of primers were designed via Primer premier 5.0 software. After abundant detections of drug resistance, specificity and sensitivity, 3 pairs of primer sets with typical primers were chosen eventually and the sequences of each pair of primer are shown in below:

(1) First Pair:

```
Upstream primer HMG1F (SEQ ID NO: 3):
5' ATGACTGCTCAAAAAGACGATAC 3'

Downstream primer HMG1R (SEQ ID NO: 4):
5' TTATTCATCACTATCTCCTACTTCT 3'
```

(2) Second Pair:

```
Upstream primer HMG1-sF (SEQ ID NO: 5):
TTCCGAAATAATCTTCTTTTAATTG

Downstream primer HMG1-sR (SEQ ID NO: 6):
TTGTGCACCGAATCGTAAATAG
```

(3) Third Pair:

```
Upstream primer HMG1-xF (SEQ ID NO: 7):
TCCCTAGGAACTTTTAAAGAGAAG

Downstream primer HMG1-xR (SEQ ID NO: 8):
TCCTTTTATTCATCACTATCTCCT
```

2. Establishment of PCR Amplification Method (1) Extraction of Total DNA from Silkworms or Silkworm Eggs The genome DNA from silkworm egg was extracted via plant DNA mini kit (DNeasy Plant mini kit) produced by QIAGEN company, and the procedure is described herein below (proceeded according to the description):

20 silkworm eggs were put in a mortar and were ground with liquid nitrogen into powder which was collected into a 1.5 mL centrifuge tube. 400 μL lysis buffer AP1 and 4 μL Rnase A were added into the centrifuge tube, and then they were mixed homogeneously in a vortex (do not mix the 400 μL lysis buffer AP1 and 4 μL Rnase A before using). The homogeneously mixed solution was incubated in 65° C. for 10 minutes (with turning the tube upside down for 2~3 times during incubation). 130 μL buffer AP2 was added, and the mixture was allowed to sit in an ice-bath for 5 minutes; then centrifuged at 14,000 rpm for 5 minutes. The supernatant was aspirated into a collecting tube of a filtration column (QIAshredder spin column), followed by centrifugation at 14,000 rpm for 2 minutes. The supernatant in the centrifuge tube was transferred to a new tube (do not stir the residue that shows up) followed by adding AP3/E with 1.5 times the volume, and they were mixed with a pipette. 650 μL mixture was transferred into an adsorption column (DNeasy Mini spin column), followed by centrifugation at 4200 rpm for 1 minute; and this step was repeated for the remaining solution. The adsorption column was put into a new collecting tube and added with 500 μL buffer AW, followed by centrifugation at 4200 rpm for 1 minute. After the supernatant was discarded, 500 μL buffer AW was added into the tube, followed by centrifugation at 14000 rpm for 2 minutes (make sure that the collecting tube won't touch the supernatant at bottom). The collecting tube was moved into a 1.5 ml or 2.0 ml centrifuge tube. 40 μL buffer AE was added for elution, then was kept at room temperature for 5 minutes, and then centrifuged at 4200 rpm for 1 minute. The above-mentioned step was repeated (i.e. 40 μL buffer AE was added for elution, then was kept at room temperature for 5 minutes, and then centrifuged at 4200 rpm for 1 minute). The extracted total DNA was stored at −20° C. in fridge for future use.

(2) Method for PCR Amplification

The 3 pairs of primers in Embodiment 1 were used to perform PCR amplification using the total DNA from silkworm or silkworm egg as template.

The PCR reaction system (with a total volume of 20 μL) is shown as below:

| | |
|---|---|
| 2× Taq Master Mix (reaction buffer) | 10 μL |
| 10 μM upstream primer HMG1F | 0.5 μL |
| 10 μM downstream primer HMG1R | 0.5 μL |
| Template DNA | 1 μL; |
| ddH$_2$O | used to fill the system up to 20 μL. |

Wherein, 2×Taq Master Mix (reaction buffer) comprises Taq DNA polymerase, 160 mM Tris-HCl, 40 mM (NH$_4$)$_2$SO$_4$, 3.0 mM MgCl$_2$ and 400 μM dNTP.

A procedure of the PCR reaction is as follows: 94° C. for 5 min; 94° C. for 30 s, 50° C. for 45 s, 72° C. for 45 s, 32 circulations; 72° C. for 10 min.

(3) Judgment of Results

First pair of primers HMG1F/HMG1R: the agarose gel electrophoresis was conducted after PCR reaction, followed by determining whether silkworm egg sample was infected by *Nosema bombycis* according to if the DNA fragments are being amplified to 561 bp or not. It was confirmed that the silkworm or silkworm egg was infected by *Nosema bombycis* when DNA fragments products were amplified to 561 bp specifically.

Second pair of primers HMG1-sF/HMG1-sR: the agarose gel electrophoresis was conducted after PCR reaction, followed by determining whether silkworm egg sample was infected by *Nosema bombycis* according to if the DNA fragments are being amplified to 684 bp or not. It was confirmed that the silkworm or silkworm egg was infected by *Nosema bombycis* when DNA fragments products were amplified to 684 bp specifically.

Third pair of primers HMG1-xF/HMG1-xR: the agarose gel electrophoresis was conducted after PCR reaction, followed by determining whether silkworm egg sample was infected by *Nosema bombycis* according to if the DNA fragments are being amplified to 251 bp or not. It was confirmed that the silkworm or silkworm egg was infected by *Nosema bombycis* when DNA fragments products were amplified to 251 bp specifically.

(4) 50 "infected" silkworm eggs (i.e. eggs oviposited by the silkworm infected by *Nosema bombycis*), healthy silkworm eggs and purified *Nosema bombycis* samples were extracted for DNA respectively, and were proceeded with PCR amplification according to the abovementioned PCR method.

Figure 2:
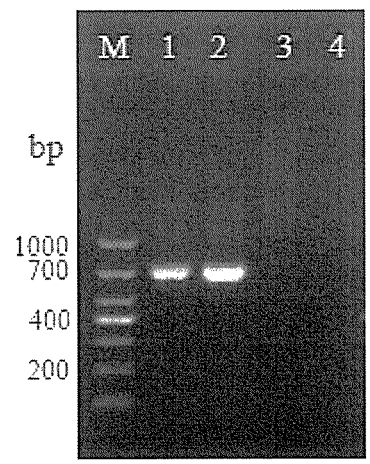
FIG. 2 shows the detection results of HMG1-sF/HMG1-sR primers. Lane M: DL1000, lane 1: infected silkworm egg DNA, lane 2: purified *Nosema bombycis* (N.b) DNA, lane 3: (healthy) pebrine-free silkworm egg DNA, lane 4: ddH$_2$O.
Figure 3:
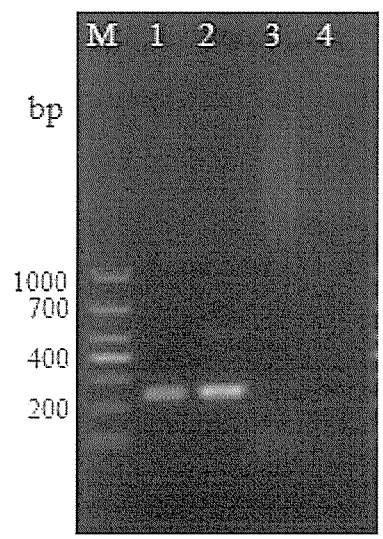
FIG. 3 shows the detection results of HMG1-xF/HMG1-xR primers. Lane M: DL1000, lane 1: infected silkworm egg DNA, lane 2: purified *Nosema bombycis* (N.b) DNA, lane 3: (healthy) pebrine-free silkworm egg DNA, lane 4: ddH$_2$O.
Figure 4:
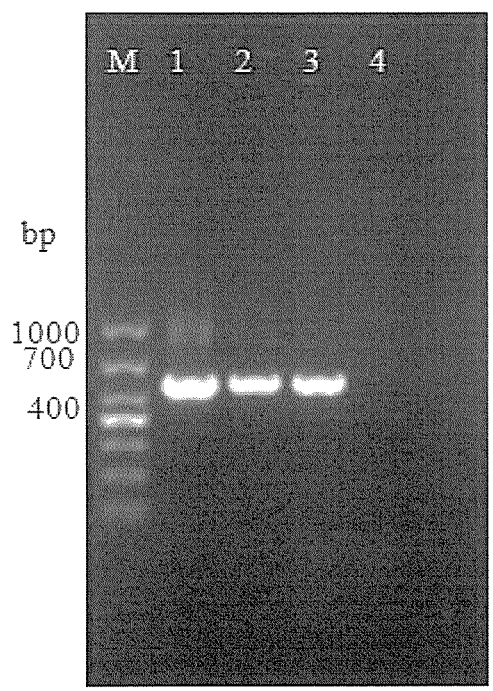
FIG. 4 shows the detection results of specificity of HMG1F/HMG1R primers. Lane M: DL1000, lane 1: N.b (*Nosema bombycis*) DNA, lane 2: N.a (*Nosema antheraeae*) DNA, lane 3: N.f (*Nosema furnacalis*) DNA, lane 4: ddH$_2$O.
Figure 5:
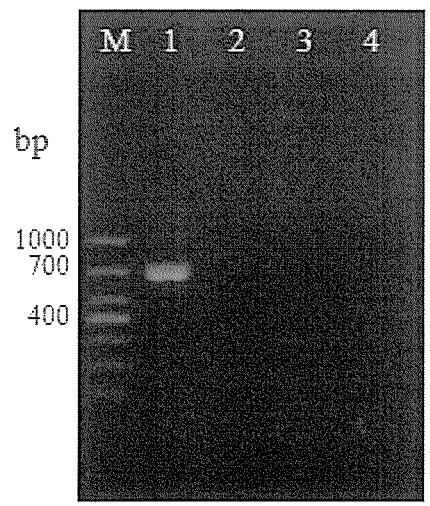
FIG. 5 shows the detection results of specificity of HMG1-sF/HMG1-sR primers. Lane M: DL1000, lane 1: N.b (*Nosema bombycis*) DNA, lane 2: N.a (*Nosema antheraeae*) DNA, lane 3: N.f (*Nosema furnacalis*) DNA, lane 4: ddH$_2$O.
Figure 6:
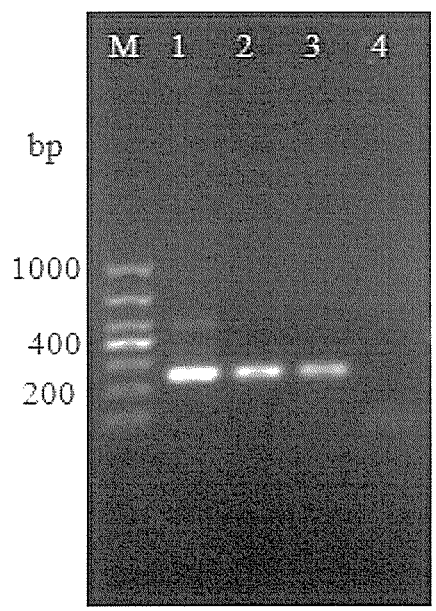
FIG. 6 shows the detection results of specificity of HMG1-xF/HMG1-xR primers. Lane M: DL1000, lane 1: N.b (*Nosema bombycis*) DNA, lane 2: N.a (*Nosema antheraeae*) DNA, lane 3: N.f (*Nosema furnacalis*) DNA, lane 4: ddH$_2$O.
Figure 7:
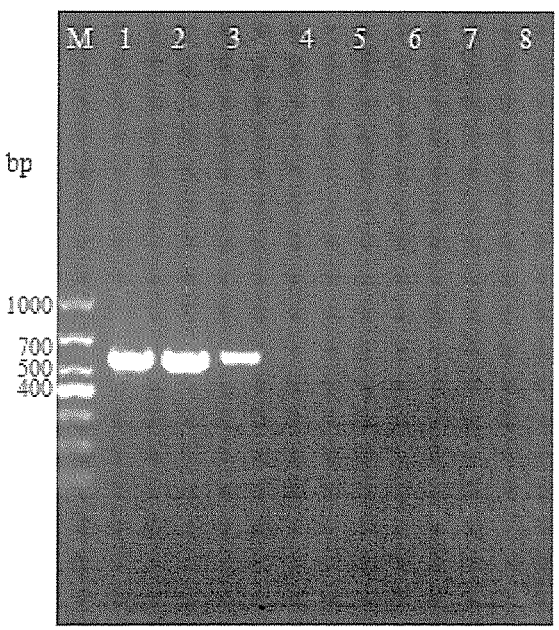
FIG. 7 shows the sensitivity detection results of HMG1F/HMG1R primers. Lane M: DL1000, lanes 1~7 refer to $5.0 \times 10^0$, $5.0 \times 10^{-1}$, $5.0 \times 10^{-2}$, $5.0 \times 10^{-3}$, $5.0 \times 10^{-4}$, $5.0 \times 10^{-5}$ and $5.0 \times 10^{-6}$ ng/μL N.b DNA respectively, and lane 8 refers to ddH$_2$O.
Figure 8:
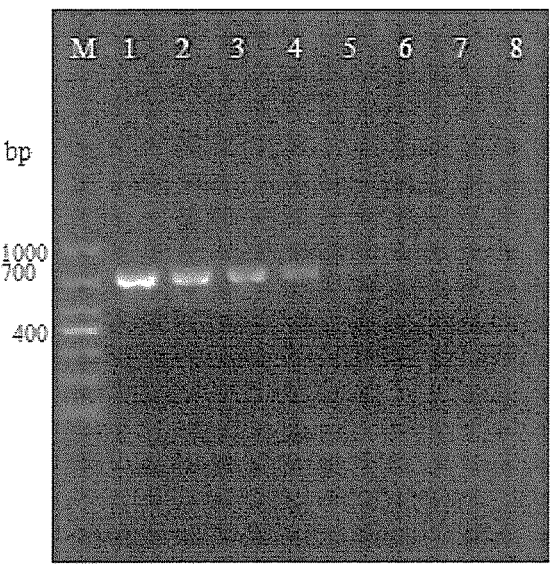
FIG. 8 shows the sensitivity detection results of HMG1-sF/HMG1-sR primers. Lane M: DL1000, lanes 1~7 refer to $5.0 \times 10^0$, $5.0 \times 10^{-1}$, $5.0 \times 10^{-2}$, $5.0 \times 10^{-3}$, $5.0 \times 10^{-4}$, $5.0 \times 10^{-5}$ and $5.0 \times 10^{-6}$ ng/μL N.b DNA respectively, and lane 8 refers to ddH$_2$O.
Figure 9:
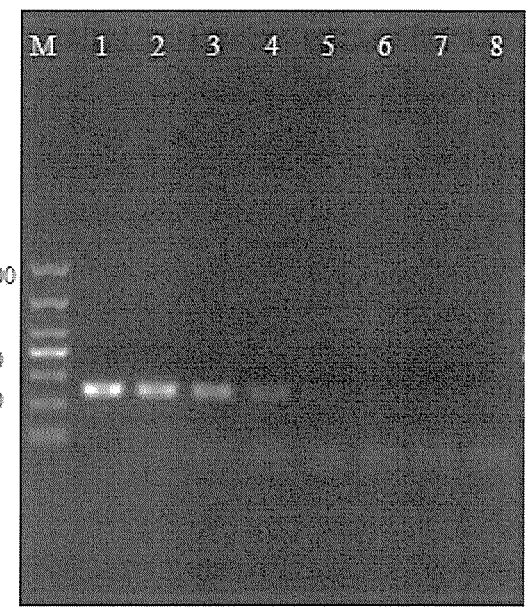
FIG. 9 shows the sensitivity detection results of HMG1-xF/HMG1-xR primers. Lane M: DL1000, lanes 1~7 refer to $5.0 \times 10^0$, $5.0 \times 10^{-1}$, $5.0 \times 10^{-2}$, $5.0 \times 10^{-3}$, $5.0 \times 10^{-4}$, $5.0 \times 10^{-5}$ and $5.0 \times 10^{-6}$ ng/μL N.b DNA respectively, and lane 8 refers to ddH$_2$O.

The detection results of agarose gel electrophoresis are shown in FIGS. 1~3 respectively. 3 pairs of primers can detect specific DNA fragments in "infected" silkworm eggs and purified *Nosema bombycis*, while no specific fragment was detected in healthy silkworm eggs. It indicates that both 3 pairs of primers and the established PCR method can be used to rapidly detect *Nosema bombycis*.

Embodiment 3. Specificity Detection of Primers

1. Using DNA of *Nosema bombycis* (N.b), *Nosema antheraeae* (N.a), *Nosema furnacalis* (N.f) as templates respectively, primers HMG1F/HMG1R, HMG1-sF/HMG1-sR and HMG1-xF/HMG1-xR were proceeded with PCR amplification by the method described in Embodiment 2, followed by the agarose gel electrophoresis to detect the results.

2. The amplification results of 3 pairs of primers are shown in FIGS. 4~6 respectively. It shows that primers HMG1-sF/HMG1-sR can detect *Nosema bombycis* specifically, while both primers HMG1F/HMG1R and primers HMG1-xF/HMG1-xR can detect all microsporidiums with great universal detectability but without specificity to *Nosema bombycis.*

Embodiment 4. Sensitivity Detection of Primers

1. DNA from *Nosema bombycis* (N.b) was extracted, and original concentration was 5.0 ng/μL.

The abovementioned N.b DNA was diluted with $ddH_2O$ for $10^0$, $10^1$, $\mathbf{10^2}$, $10^3$, $10^4$, $10^5$ and $10^6$ tunes. The obtained concentration gradients were $5.0\times10^0$, $5.0\times10^{-1}$, $5.0\times10^{-2}$, $5.0\times10^{-3}$, $5.0\times10^{-4}$, $5.0\times10^{-5}$ and $5.0\times10^{-6}$ ng/μL.

2. Using the abovementioned N.b DNA in various concentrations as templates, primers HMG1F/HMG1R, HMG1-sF/HMG1-sR and HMG1-xF/HMG1-xR were proceeded with PCR amplification by the method described in Embodiment 2, followed by the agarose gel electrophoresis to detect the results.

3. The amplification results of 3 pairs of primers are shown in FIGS. 7~9 respectively. It shows that both primers HMG1F/HMG1R and primers HMG1-sF/HMG1-sR can detect N.b DNA in concentration of $5.0\times10^{-4}$ ng/μL with great detection sensitivity, while primers HMG1-xF/HMG1-xR can only detect N.b DNA in $5.0\times10^{-3}$ ng/μL of which the sensitivity is one order of magnitude less than the other two pairs.

Thus, in conclusion, from the aspects of specificity and sensitivity, only primers HMG1-sF/HMG1-sR can detect *Nosema bombycis* specifically with great detection sensitivity, and in particular can detect *Nosema bombycis* in silkworm eggs, which provide guarantees for detection of "infected" silkworm eggs in silkworm eggs production and for safe distribution of silkworm eggs, and have major significance in practical detection of *Nosema bombycis* and detection application in immature silkworm eggs being infected by *Nosema bombycis* or not. The experimental result shows that HMG1 gene is an excellent molecular target for detection of *Nosema bombycis.*

In addition, only primers HMG1F/HMG1R can detect various microsporidiums universally with great detection sensitivity, and have extensive application value and significance in practical detections of various microsporidiums.

Embodiments herein below are further detections of primers HMG1F/HMG1R for their applicability and sensitivity.

Embodiment 5. Detections of Mid-Gut of Fourth Instar Larvae of the Silkworm Infected by N.b for Different Durations and Silkworm Eggs Infected by N.b 1. Extraction of Total RNA RNAs of mid-gut of fourth instar larvae of the silkworm infected by N.b for different durations and silkworm eggs infected by N.b were extracted respectively via EASYspin plant RNA rapid extraction kits from Aidlab Biotechnologies Company according to the instruction thereof. Specific steps are described herein below:

(1) 500 μL lysate RLT was transferred to 1.5 mL centrifuge tube and mixed homogeneously after adding 50 μL plant RNA co-extraction agent (PLANTaid, combined with polysaccharide polyphenol) for future use.

(2) The silkworm tissue, in liquid nitrogen, was ground into powder of which 50 mg was transferred to said centrifuge tube containing lysate RLT and PLANTaid, followed by immediate vigorous shaking by hand for 20 second to sufficient lysis.

(3) The lysate was centrifuged at 13000 rpm for 5~10 minutes in order to precipitate fragments that can't be lysed and the PLANTaid combined with polysaccharide polyphenol.

(4) Supernatant of lysate was transferred to a new centrifuge tube; after adding absolute ethyl alcohol with half volume of the supernatant (at this moment, there might be sediment which would not interfere with the extraction process), mix them immediately by pipetting and do not process the centrifugation.

(5) The mixture was added in an adsorption column RA (each addition was less than 720 μL and two additions were made if it's too much), (the adsorption column was put into a collecting tube) and was centrifuged at 13000 rpm for 2 minutes, followed by discarding the effluent.

(6) 700 μL de-protein liquid RW1 was added, then placed at room temperature for 1 minute, and then centrifuged at 13000 rpm for 30 s. Afterwards, the effluent was discarded.

(7) 500 μL wash liquid RW was added, and then centrifuged at 13000 rpm for 30 s. Afterwards, the effluent was discarded. 500 μL wash liquid RW was added to the mixture again and the operations described above were repeated once.

(8) The adsorption column RA was put into an empty collecting tube and centrifuged at 13000 rpm for 2 minutes in order to remove the wash liquid as much as possible, so as to avoid the residual ethyl alcohol in wash liquid inhibiting downstream reaction.

(9) The adsorption column RA was fetched and put into an RNase centrifuge tube, followed by adding 30~50 μL sterile water (RNase free water, heated in 70~90° C. in advance to increase the yield) which can remove RNA enzyme, to a central part of adsorption film according to the prospected RNA yield, and then it was centrifuged at 12000 rpm for 1 minute after being placed at room temperature for 1 minute.

2. RNA Reverse Transcription to cDNA

The reverse transcription reaction of extracted RNA was proceeded using PrimeScript™ RT reagent Kit with gDNA Eraser (Perfect Real Time) kit produced by TAKARA company. The steps are as follows:

(1) Reaction of Removal of DNA Genome
Reaction System (20 μL):

| | |
|---|---|
| 5× gDNA Eraser Buffer | 4.0 μL |
| gDNA Eraser | 1.0 μL |
| Total RNA | ≤2.0 μg |
| RNase Free dH2O | added to make the system up to 20 μL |

Reaction condition of removal of DNA genome: 42° C. for 2 min (or at room temperature for 5 min, maximum for 30 min).

(2) Reverse Transcription Reaction
Reverse Transcription System (40 μL):

| | |
|---|---|
| Reaction liquid from step (1) | 20 μL |
| 5× primeScript Buffer2 | 4.0 μL |
| PrimeScript RT Enzyme Mix I | 2.0 μL |
| RT Primer Mix | 2.0 μL |
| RNase Free dH2O | added to make the system up to 40 μL. |

Reaction condition of reverse transcription: 37° C. for 15 min; 85° C. for 5 s; store at 4° C./−20° C. for future use.

3. PCR Detection

RT-PCR reaction was proceeded by specific primers HMG1F/HMGR using respective cDNA from step (2) as templates.

Figure 10:
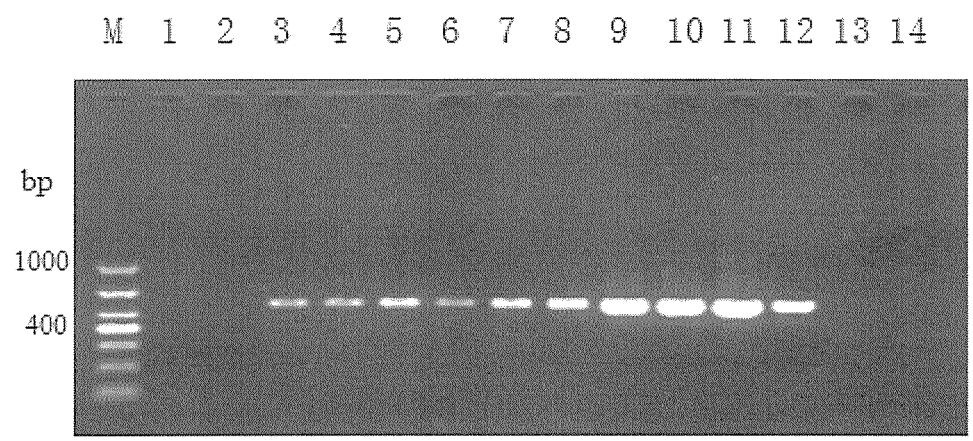
FIG. 10 shows the PCR results of HMG1F/HMG1R primers for cDNA templates from fourth instar larvae of the silkworm infected by N.b for different durations. Lane M: DL1000, lane 1: 6 h, lane 2: 12 h, lane 3: 18 h, lane 4: 24 h, lane 5: 36 h, lane 6: 48 h, lane 7: 60 h, lane 8: 72 h, lane 9: 84 h, lane 10: 96 h, lane 11: 108 h, lane 12: purified N.b cDNA, lane 13: healthy silkworm mid-gut cDNA, lane 14: ddH$_2$O.

The result of reaction is shown in FIG. 10, HMG1 gene had not been detected during the infection of N.b in silkworm mid-gut for the former 12 h, which indicated that no microsporidium began to propagate, while HMG' gene had transcriptional activity since the infection for 18 h, which indicated that the microsporidiums have possibly begun the reproduction and division. Thus this conclusion is consistent with the biocycle of *Nosema bombycis* infecting silkworm in prior art, which laterally verifies that the detection primers described in present invention have excellent specificity and sensitivity.

Embodiment 6. Detections of cDNA Templates from Silkworm Egg Infected by N.b for Different Duration 1. In the present embodiment, both silkworm eggs infected by N.b and healthy silkworm egg were detected respectively, using cDNA from silkworm eggs which were infected by N.b for different durations without acid dipping, before acid dipping and after acid dipping as templates respectively, and using DNA from healthy silkworm egg as control, to proceed PCR detection by primers HMG1F/HMG1R.

2. Experimental Method (1) Sampling before acid dipping: after silkworms were infected by *Nosema bombycis*, the silkworm eggs were taken respectively when silkworms mated for 2 h, 8 h, 10 h, 12 h and 17 h, then the silkworm eggs were stored at −80° C. fridge for future use.

(2) Acid dipping: after an egg circle was divided into two parts, about 20 h after oviposition, the silkworm eggs were dipped in acid (proportion of hydrochloric acid was 1.075) with an acid dipping condition as follows: acid dipped at 46° C. for 5 minutes and washed with water for 20 minutes. Then they were stored in an artificial climate incubator at 25° C., 85% humidity for incubating to newly-hatched silkworms.

(3) 24 h, 48 h, 72 h, 96 h, 120 h, 144 h, 168 h, 192 h, 216 h and 240 h (newly-hatched silkworm) after oviposition, silkworm eggs after acid dipping as well as silkworm eggs without acid dipping were sampled respectively and stored at −80° C. fridge for future use.

3. Results are shown as FIGS. 11~13.

Figure 11:
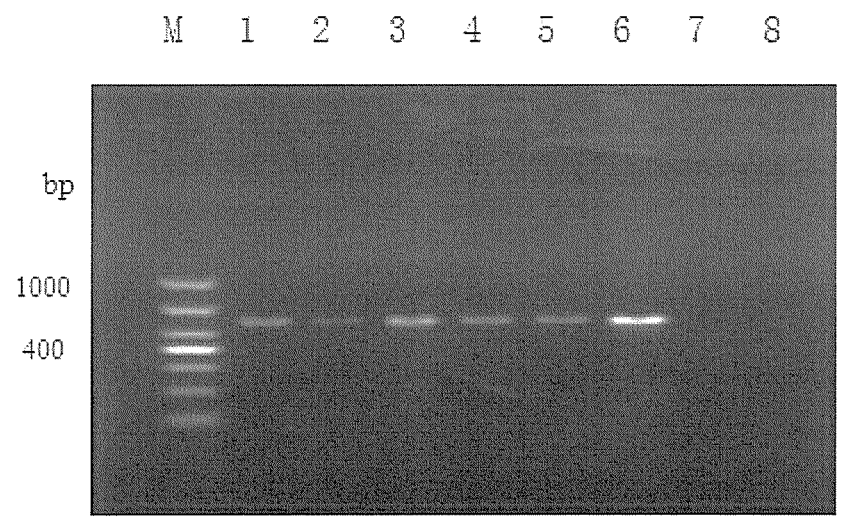
FIG. 11 shows the PCR results of HMG1F/HMG1R primers for cDNA templates from silkworm eggs infected by N.b (before acid dipping) for different durations. Lane M: DL1000, lane 1: 2 h, lane 2: 8 h, lane 3: 10 h, lane 4: 12 h, lane 5: 17 h, lane 6: purified N.b spore cDNA, lane 7: healthy silkworm egg cDNA, lane 8: ddH$_2$O.

FIG. 11 shows the PCR result of primers HMG1F/HMG1R for cDNA templates from silkworm eggs infected by N.b (before acid dipping) for different durations. Lane M was DL1000; lane 1: 2 h; lane 2: 8 h; lane 3: 10 h; lane 4: 12 h; lane 5: 17 h; lane 6: purified cDNA of N.b spore; lane 7: cDNA of healthy silkworm egg; lane 8: ddH$_2$O.

Figure 12:
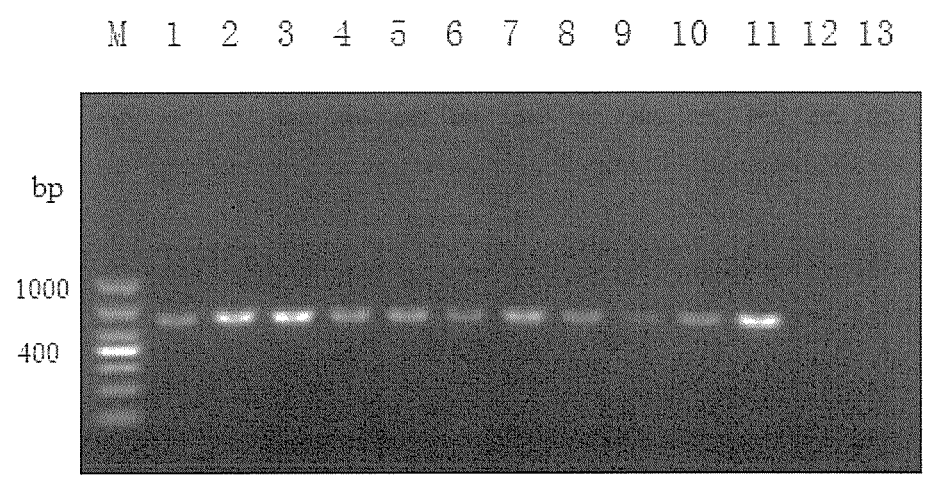
FIG. 12 shows the PCR results of HMG1F/HMG1R primers for cDNA templates from silkworm eggs infected by N.b (without acid dipping) for different durations. Lane M: DL1000, lane 1: 24 h, lane 2: 48 h, lane 3: 72 h, lane 4: 96 h, lane 5: 120 h, lane 6: 144 h, lane 7: 168 h, lane 8: 192 h, lane 9: 216 h, lane 10: 240 h, lane 11: purified N.b cDNA, lane 12: healthy silkworm egg cDNA, lane 13: ddH$_2$O.

FIG. 12 shows the PCR result of primers HMG1F/HMG1R for cDNA templates from silkworm eggs infected by N.b (without acid dipping) for different durations. Lane M was DL1000; lane 1: 24 h; lane 2: 48 h; lane 3: 72 h; lane 4: 96 h; lane 5: 120 h; lane 6: 144 h; lane 7: 168 h; lane 8: 192 h; lane 9: 216 h; lane 10: 240 h; lane 11: purified cDNA of N.b spore; lane 12: cDNA of healthy silkworm egg; lane 13: ddH$_2$O.

Figure 13:
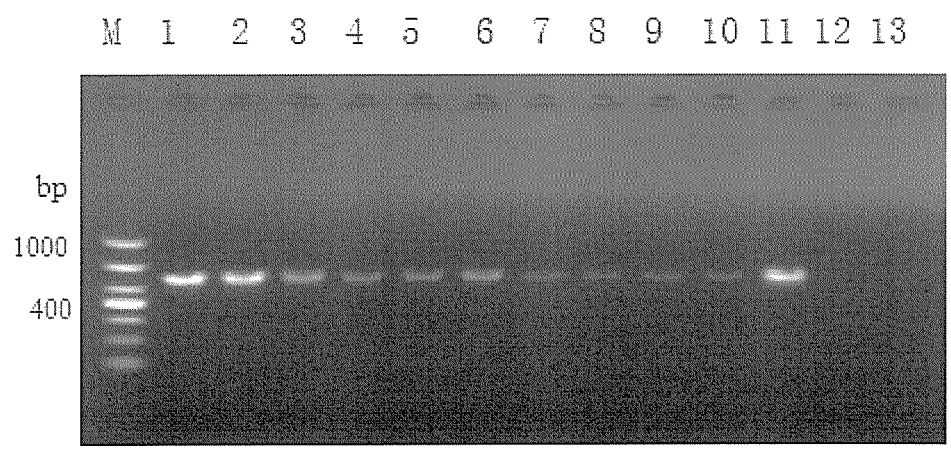
FIG. 13 shows the PCR results of HMG1F/HMG1R primers for cDNA templates from silkworm eggs infected by N.b (with acid dipping) for different durations. Lane M: DL1000, lane 1: 24 h, lane 2: 48 h, lane 3: 72 h, lane 4: 96 h, lane 5: 120 h, lane 6: 144 h, lane 7: 168 h, lane 8: 192 h, lane 9: 216 h, lane 10: 240 h, lane 11: purified N.b cDNA, lane 12: healthy silkworm egg cDNA, lane 13: ddH$_2$O.

FIG. 13 shows the PCR result of primers HMG1F/HMG1R for cDNA templates from silkworm eggs infected by N.b (with acid dipping) for different durations. Lane M was DL1000; lane 1: 24 h; lane 2: 48 h; lane 3: 72 h; lane 4: 96 h; lane 5: 120 h; lane 6: 144 h; lane 7: 168 h; lane 8: 192 h; lane 9: 216 h; lane 10: 240 h; lane 11: purified cDNA of N.b spore; lane 12: cDNA of healthy silkworm egg; lane 13: ddH$_2$O.

Detection results from FIGS. 11~13 show that, 2 h after oviposition, HMG1 gene can be detected with reverse transcription activity. Furthermore, HMG1 gene has reverse transcription activity during the whole process of development of silkworm eggs (both with acid dipping and without acid dipping) hereafter. Therefore, HMG1 gene can serve as a molecular target to detect whether the immature silkworm egg was infected by *Nosema bombycis* or not.

In conclusion, the detection primers and the kit of the present invention can determine accurately whether the sample contains *Nosema bombycis* or not and in particular can detect *Nosema bombycis* in silkworm eggs, which provide guarantees for detection of "infected" silkworm eggs and for safe distribution of silkworm eggs. The experimental result also shows that HMG1 gene is an excellent molecular target for detecting microsporidium.

What is claimed:

1. An isolated cDNA consisting of a full-length nucleotide sequence shown in SEQ ID NO:2.

* * * * *